US00PP16941P2

(12) United States Plant Patent
Olesen

(10) Patent No.: US PP16,941 P2
(45) Date of Patent: Aug. 8, 2006

(54) SHRUB ROSE PLANT NAMED 'POULCOT005'

(50) Latin Name: *Rosa* hybrid
Varietal Denomination: Poulcot005

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 42 days.

(21) Appl. No.: 11/090,138

(22) Filed: Mar. 24, 2005

(51) Int. Cl.
*A01H 5/00* (2006.01)

(52) U.S. Cl. ..... Plt./107
(58) Field of Classification Search ..... Plt./107
See application file for complete search history.

*Primary Examiner*—Kent Bell
*Assistant Examiner*—Annette H Para

(57) ABSTRACT

A new garden rose plant of the shrub rose class which has abundant, pink, single petal flowers and attractive foliage. This new and distinct variety has shown to be uniform and stable in the resulting generations from asexual propagation.

3 Drawing Sheets

Botanical designation: *Rosa* hybrid.
Variety denomination: 'Poulcot005'.

SUMMARY OF THE INVENTION

The present invention constitutes a new and distinct variety of garden rose plant that originated from a controlled crossing between the female seed parent, an unnamed seedling, and the male pollen parent 'Pouldiram', U.S. Plant Pat. No. 12,568.

The two parents were crossed during the summer of 1995, and the resulting seeds were planted in a controlled environment in Fredensborg, Denmark. The new variety, named 'Poulcot005', is a single selection from the seedlings which resulted from the stated cross.

The new variety may be distinguished from the female seed parent by the following combination of characteristics:

1. The seed parent has light pink flowers, while 'Poulcot005' has deep pink flowers.
2. The seed parent has a petal count of 12 to 18, while 'Poulcot005' has 7 petals.

The new variety may be distinguished from its male pollen parent from the following combination of characteristics:

1. 'Pouldiram' has white flowers, while 'Poulcot005' has deep pink flowers.
2. 'Pouldiram' has a taller growth habit than 'Poulcot005'.

The objective of the hybridization of this rose variety was to create a new and distinct variety for garden use with unique qualities, such as:

1. Uniform and abundant pink, single petal, flowers;
2. Vigorous, but compact growth when propagated both as a budded rose and on its own roots;
3. Disease resistance;
4. Continuous bloom through the growing season;
5. Abundant rose hips.

This combination of qualities is not present in previously available commercial cultivars of this type, known to the inventor, and distinguish 'Poulcot005' from all other varieties of which we are aware.

As part of the rose development program, Mogens N. Olesen germinated the seeds from the aforementioned hybridization during winter of 1995 and conducted evaluations on the resulting seedlings in a controlled environment in Fredensborg, Denmark.

'Poulcot005' was selected in the spring of 1996 by the inventor as a single plant from the progeny of the aforementioned hybridization.

Asexual reproduction of 'Poulcot005' by traditional budding and rooted cuttings was first done by Mogens N. Olesen in the nursery in Fredensborg, Denmark in July 1996. This initial and other subsequent asexual propagations conducted in controlled environments have demonstrated that the characteristics of 'Poulcot005' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcot005'. Specifically illustrated in the drawings:

FIG. 1.2; Cluster of flowers upon opening;

FIG. 1.3; Flower buds;

FIG. 1.4; Sepals detached, and flower with petals removed, showing reproductive flower parts;

FIG. 1.5; Flower petals detached;

FIG. 2.2; Mature foliage;

FIG. 2.3; Juvenile and mature bare stems exhibiting thorns;

DETAILED DESCRIPTION OF THE VARIETY

Figure 1:
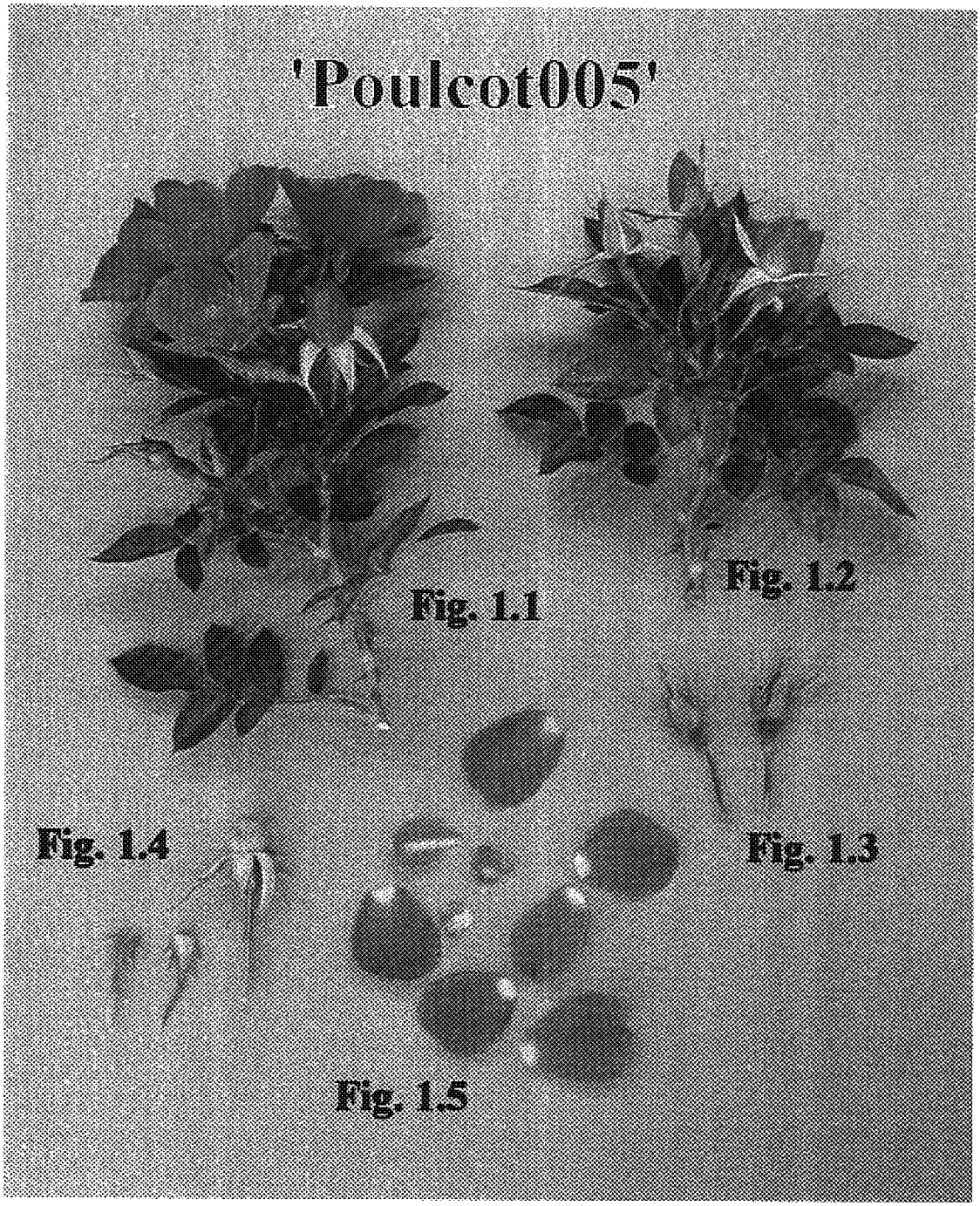
FIG. 1.1; Cluster of open flowers showing branching, and the attachment of leaves, buds, and pedicels.

The following is a description of 'Poulcot005', as observed in its growth in a field nursery in Jackson County, Oreg. Observed plants are 2 years of age, and were grown on *Rosa multiflora* understock. Color references are made using The Royal Horticultural Society (London, England) Colour Chart, 2001, except where common terms of color are used.

For a comparison, several physical characteristics of the rose varieties 'Poulcot004', U.S. Plant patent application Ser. No. 11/001,947, and 'Poulrijk', U.S. Plant Pat. No. 12,519 are compared to 'Poulcot005' in Chart 1.

CHART 1

| | 'Poulcot005' | 'Poulcot004' | 'Poulrijk' |
|---|---|---|---|
| General tonality | Red-Purple Group 58B with intonations of Red-Purple Group N57A. | Red-Purple Group 57A to 57B | Red-Purple Group 58C |
| Petalage | 7 petals | 5 to 7 petals | 20 to 25 petals |
| Petal spot, upper surface | Yellow 3A | White 155B. Green-White Group 157A at point of attachment. | White 157D. |

FLOWER AND FLOWER BUD

Blooming habit: Continuous.

Flower bud:

*Size.*—Upon opening, 16 mm in length from base of receptacle to end of bud. Bud diameter is 6 mm.

*Bud form.*—Ovate.

*Bud color.*—As sepals unfold, petals are Red Group 52A to 52B.

*Sepal inner surface.*—Color: Yellow-Green Group 145A to Yellow-Green Group 147D. Weak Anthocyanic pigments Greyed-Red Group 181B observed. Surface: Weak to medium pubescence observed.

*Sepal outer surface.*—Color: Yellow-Green Group 144A. Anthocyanic pigments Greyed-Purple Group 185A. Texture: Somewhat rough with stipitate glands.

*Sepal shape.*—Apex: Cirrhose. Base: Flat at union with receptacle.

*Sepal margin.*—Margins have medium foliaceous appendages on three of the five sepals.

*Sepal size.*—22 mm (l)×6 mm (w).

*Receptacle.*—Texture: Smooth, lightly pubescent and glaucous. Shape: Elliptical. Size: 6 mm (h)×4 mm (w). Color: Green Group 138B. Anthocyanic pigments the color of Greyed-Purple Group 187B observed.

*Peduncle.*—Surface: Smooth with thorns. Length: 16 cm on average. Diameter: Normally 3.5 mm. Color: Yellow-Green Group 146B.

*Pedicel.*—Surface: Slightly rough with stipitate glands. Length: 15 mm on average. Diameter: Normally 1.5 to 2 mm. Color: Yellow-Green Group 144B. Anthocyanic pigments the color of Greyed-Purple Group 183A observed. Strength: Weak. Scent: Stipitate glands release strong spicy scent when touched.

Flower bud development: Flower buds are borne in clusters of 5 to 11 flower buds. Inflorescence type resembles a corymb.

Flower bloom:

*Fragrance.*—None.

*Duration.*—The blooms have a duration on the plant of approximately 4 to 7 days. Afterwards, petals fall cleanly away from plant.

*Size.*—Flower diameter is 40 mm when open. Flower depth is 10 mm.

*Flower shape.*—Single, fully open and almost flat.

*Petalage.*—Typically, flowers have 7 petals total, 1 of which is a petaloid.

*Petal color.*—Upon opening: Upper surface: Red-Purple Group 58B with intonations of Red Group 52A. Occasional streaks of Red Group 52D or Yellow Group 8C observed. Lower surface: Red-Purple Group 58B with intonations of Red Group 52A. Occasional streaks of Red Group 52D or Yellow Group 8C observed. Basal petal spots, upon opening: Upper surface: Yellow Group 3A. Lower surface: Yellow Group 3C. After opening: Upper surface: Red-Purple Group 58C. Lower surface: Red-Purple Group 58B. Occasional streaks the color of Red Group 52D and Yellow Group 8C observed. Basal petal spots, after opening: Upper surface: Yellow Group 3A. Lower surface: Yellow Group 3C.

General tonality: On open flower Red-Purple Group 57B to 58C with intonations of Red-Purple Group N57A. No changes in general tonality occur.

Petals:

*Petal reflex.*—Flat.

*Margin.*—Entire, with occasional cleft and point at the center observed.

*Shape.*—Generally narrow elliptical. Apex: Rounded. Base: Acute.

*Size.*—22 mm (l)×18 mm (w).

*Texture.*—Smooth.

*Thickness.*—Thin.

*Arrangement.*—Not Formal.

Petaloids:

*Size.*—16 mm (l)×9 mm (w).

*Shape.*—Narrow elliptical to asymmetrical. Base: Very acute. Apex: Round with cleft. Color: Red-Purple Group 58C.

Reproductive organs:

*Pollen.*—Quantity: Small amount. Color: Greyed-Orange 163A.

*Anthers.*—Size: 1.5 mm in length. Color: Greyed-Orange Group 163A. Quantity: 95 average.

*Filaments.*—Color: Yellow-Orange Group 21B. Length: 6 mm.

*Pistils.*—Length: 4 to 5 mm. Quantity: 18.

*Stigmas.*—Superior in location relative to the length of the filaments and the height of the anthers. Color: Yellow-Green Group 145C to 145D.

*Styles.*—Color: Yellow-Green Group 145C to 145D.

*Hips.*—Color: Greyed-Orange Group 169A. Size: Typically 14 mm (l)×13 mm (w). Shape: Rounded to somewhat elliptical.

*Seeds.*—Quantity: 15 to 20 observed. Size: 5 mm (l)×3 mm (w). Color: Greyed-Yellow Group 162B.

PLANT

Plant growth: Spreading and low growing. When grown as a budded field grown plant on *Rosa multiflora* understock, the average height of the plant is 40 cm and the average width is 40 to 50 cm.

Stems:

*Color.*—Juvenile growth: Yellow-Green Group 144B. Anthocyanic intonations of Greyed-Purple Group 185C. Mature growth: Yellow-Green Group 146C.

*Length.*—On average, canes are 30 cm from the base of the plant to the flowering portion.

*Diameter.*—7 mm.

*Internodes.*—On mature canes, there is an average distance of 32 mm between nodes.

*Surface texture.*—Young wood: Rough with small prickles. Older wood: Smooth.

Thorns:

*Incidence.*—15 to 20 thorns per 10 cm of stem on average.

*Size.*—8 mm.

*Shape.*—Upper side: Flat. Lower side: Deeply concave.

*Color.*—Juvenile thorns: Greyed-Red Group 179A to Greyed-Red Group 181A. Mature thorns: Greyed-Yellow-group 160A.

Plant foliage: Normal number of leaflets leaves in middle of the stem: 7 leaflets.

*Compound leaf.*—70 to 83 mm (l)×36 to 50 (w).

*Quantity.*—3 leaves per 10 cm of stem on average.

*Color of mature foliage.*—Upper side: Yellow-Green Group 147A. Lower side: Yellow-Green Group 147B.

*Color of juvenile foliage.*—Upper side: Yellow-Green Group 144A. Lower side: Yellow-Green Group 144B. Anthocyanic intonations Greyed-Red Group 178A.

Plant leaves and leaflets:

*Stipules.*—Size: 13 mm in length. Quantity: 2 per compound leaf. Shape: Linear, slightly broad based with outward extending apecies. Margins: Finely serrated with many stipitate glands. Color: Yellow-Green Group 146A.

*Petiole.*—Length: 14 mm. Diameter: 2 mm. Upper surface: Color: Yellow-Green Group 146A occasionally exhibiting Greyed-Purple Group 185A. Observations: Few stipitate glands at margins.

*Lower surface.*—Color: Yellow-Green Group 146C.

*Rachis.*—Length: 40 mm. Upper surface: Color: Yellow-Green Group 146A occasionally exhibiting Greyed-Purple Group 185A. Observations: Few stipitate glands. Lower surface: Color: Yellow-Green Group 146C. Observations: Few small prickles.

*Leaflet.*—Edge: Serrated. Size: Average size of the terminal leaflet on normal leaves is 31 mm (l)×18 mm (w). Shape: Elliptical to ovate. Base: Obtuse. Apex: Acuminate. Texture: Smooth. Thickness: Thick. Arrangement: Odd pinnate. Venation: Reticulate. Glossiness: Moderately glossy.

Disease resistance: Above average resistance to mildew, rust, black spot, and Botrytis under normal growing conditions in Jackson County, Oreg.

Cold hardiness: The variety 'Poulcot005' has been found to be cold tolerant to USDA Cold Hardiness Zone 6.

Heat tolerance: 'Poulcot005' has been found to be suitable to climate conditions described in zone 7 of the American Horticulture Society Heat Zone map.

It is claimed:

1. A new and distinct variety of rose plant of the shrub rose class named 'Poulcot005', illustrated and described herein, due to its abundant pink, single petal flowers, compact growth habit, disease resistance, and extended period of bloom.

* * * * *

'Poulcot005'
Fig. 1.1
Fig. 1.2
Fig. 1.3
Fig. 1.4
Fig. 1.5

Figure 2:
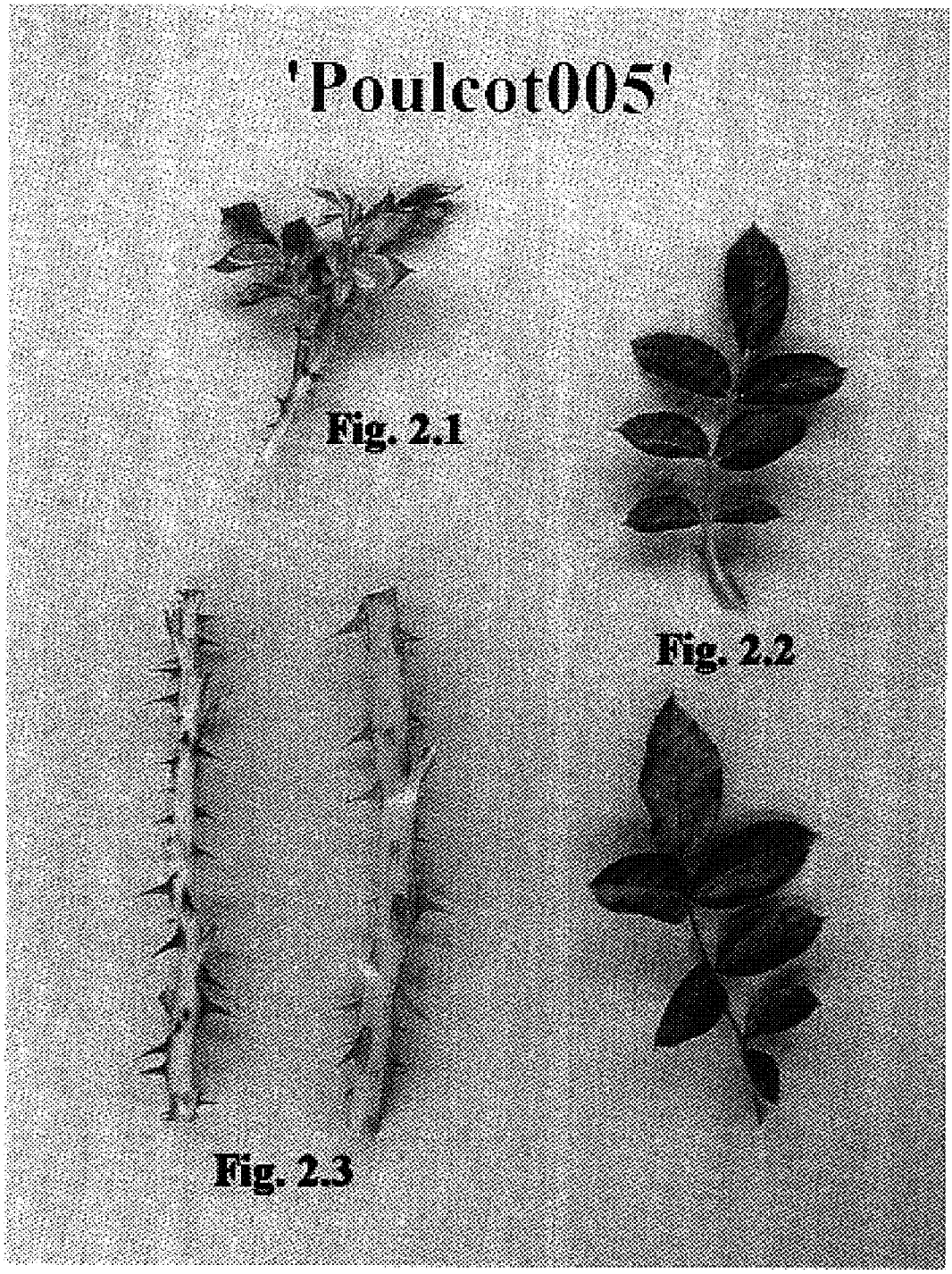
FIG. 2.1; Juvenile foliage attached to stem.
Figure 3:
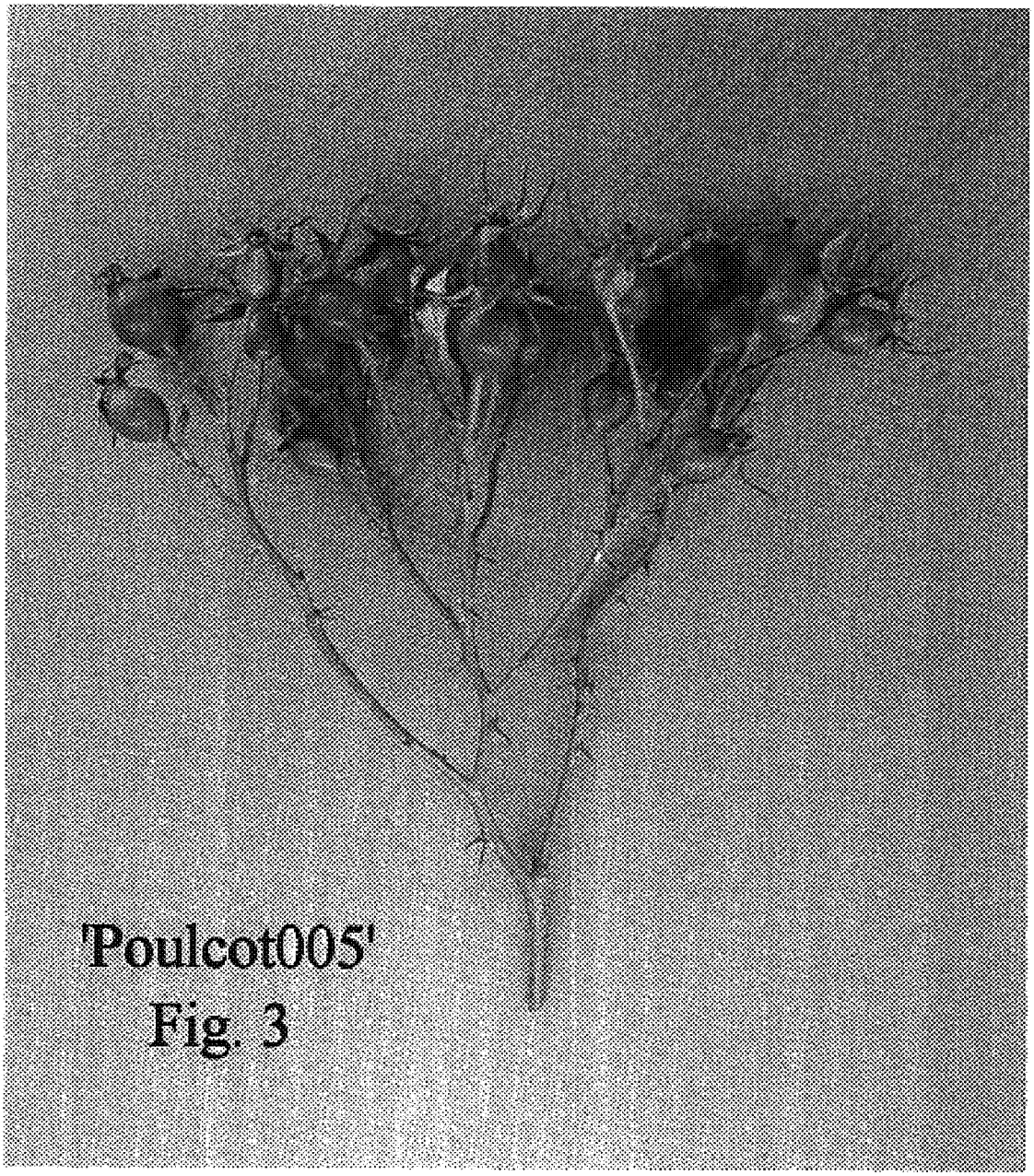
FIG. 3; Rose hips attached to the stem, showing characteristics of the rose hips, as well as the type of inflorescence.

'Poulcot005'
Fig. 2.1
Fig. 2.2
Fig. 2.3

'Poulcot005'